United States Patent [19]

Koike et al.

[11] Patent Number: 4,992,451

[45] Date of Patent: Feb. 12, 1991

[54] 1,4-DIHYDROPYRIDINE DERIVATIVES

[75] Inventors: Hiroyuki Koike; Hiroshi Nishino; Masafumi Yoshimoto, all of Tokyo, Japan

[73] Assignee: Sankyo Company, Limited, Tokyo, Japan

[21] Appl. No.: 324,981

[22] Filed: Mar. 14, 1989

Related U.S. Application Data

[63] Continuation of Ser. No. 146,713, Jan. 21, 1988, abandoned, which is a continuation of Ser. No. 873,946, Jun. 13, 1986, abandoned.

[30] Foreign Application Priority Data

Jun. 14, 1985 [JP] Japan ............................ 60-128346

[51] Int. Cl.$^5$ ................ C07D 401/12; A61K 31/445
[52] U.S. Cl. ................................. 514/318; 546/194; 546/310; 514/352
[58] Field of Search ............... 546/194, 310; 514/318, 514/352

[56] References Cited

U.S. PATENT DOCUMENTS

| | | | |
|---|---|---|---|
| 3,775,422 | 11/1973 | Bosset et al. | 546/321 |
| 3,935,223 | 1/1976 | Meyer et al. | 546/310 |
| 4,448,964 | 5/1984 | Muto et al. | 546/194 |
| 4,472,411 | 9/1984 | Hatayama et al. | 546/321 |
| 4,565,824 | 1/1986 | Wehinger et al. | 546/321 |
| 4,579,859 | 4/1986 | Ueda et al. | 546/321 |
| 4,603,135 | 7/1986 | Meguro et al. | 546/321 |

FOREIGN PATENT DOCUMENTS

| | | |
|---|---|---|
| 125803 | 11/1984 | European Pat. Off. . |
| 1173862 | 12/1969 | United Kingdom . |
| 1455502 | 11/1976 | United Kingdom . |

Primary Examiner—Jane T. Fan
Attorney, Agent, or Firm—Frishauf, Holtz, Goodman & Woodward

[57] ABSTRACT 1,4-Dihydro-6-methyl-4-(substituted phenyl)pyridine-3,5-dicarboxylic acid esters have an amino group at the 2-position and at least one nitrooxy group in at least one of the ester groups. These compounds have a variety of valuable activities, including antihypertensive and $Ca^{++}$-blocking activities, leading to their use for the treatment of circulatory and coronary disorders. They may be prepared by condensation of appropriate substituted acetic acid esters.

11 Claims, No Drawings

1,4-DIHYDROPYRIDINE DERIVATIVES

This application is a continuation of application Ser. No. 07,146,713, filed Jan. 21, 1988, now abandoned which is a continuation of U.S. Ser. No. 06/873,946 filed June 13, 1986 (abandoned).

BACKGROUND OF THE INVENTION

The present invention relates to a series of new 4-(substituted phenyl)-1,4-dihydropyridine derivatives characterized by having an amino group at the 2-position and esterified carboxy groups at the 3- and 5-positions, at least one of the ester groups containing a nitrooxy group as substituent. The compounds of the invention have been found to have valuable therapeutic activities, especially in the treatment of circulatory disorders. The invention thus also provides for the pharmaceutical use of such compounds and, of course, for their preparation.

Circulatory and coronary disorders are amongst the major causes of death in the industrialized world and, even where they do not result in death, disablement or a severe curtailment of lifestyle may result. Notwithstanding this, the full etiology of such disorders has not been resolved, even though certain factors, notably genetic and dietary factors, have been implicated There is, therefore, a substantial need for medicines to treat this ma)or problem. In attempting to treat circulatory and coronary disorders, attention has been focused on a variety of different metabolic pathways and the drugs used in such treatment have a variety of different structures, depending upon the particular metabolic pathway which it is desired to influence.

Of the many classes of drug proposed for use in such treatment, some compounds have a 4-(substituted phenyl)-1,4-dihydropyridine basic structure and, included within such general classes of drug are Nifedipine (which is included amongst the compounds disclosed in British patent Specification No. 1,173,862) and Nicardipine (which is included amongst the compounds disclosed in British patent Specification No. 1,455,502). Other related compounds have more recently been described in U.S. Pat. No. 4,472,411. All of these compounds have in common a 4-(nitrophenyl)-2,6-dimethyl-1,4-dihydropyridine-3,5-dicarboxylic acid ester structure.

We have now discovered that the inclusion of a nitrooxy substituent on at least one of the ester parts of the molecule and the replacement of the methyl group at the 2-position by an amino group leads to the production of a series of novel compounds which, surprisingly, have activities better than those of the known compounds, notably better than Nifedipine. Moreover, the compounds of the invention have unexpectedly been found to exhibit lower toxicity (at least, in test animals) and an activity which not only is longer lasting but also develops more slowly (thus avoiding problems which can arise from sudden vasodilation or reduction in blood pressure). A combination of the two structural changes mentioned above is necessary in order to achieve the desirable results of the present invention.

The compounds of the invention have been found to have excellent antihypertensive activity and activity as a $Ca^{++}$ channel blocker, leading, inter alia, to the possibility of use as a vasodilator. In both of these activities, the compounds of the invention have demonstrated, in preliminary tests, activities significantly better than those of the prior art, notably Nifedipine.

BRIEF SUMMARY OF INVENTION

It is, therefore, an object of the present invention to provide, as a novel composition of matter, a series of new 4-(substituted phenyl)-1,4-dihydropyridine derivatives.

It is a further object of the invention to provide such compounds having valuable activities for the treatment of circulatory and coronary disorders.

It is a further object of the invention to provide for the use of such compounds in such treatment.

The compounds of the present invention are those compounds of formula (I):

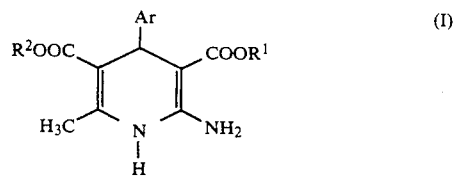

wherein:

Ar represents a phenyl group having one or two substituents independently selected from the group consisting of $C_1$–$C_4$ alkyl groups, $C_1$–$C_4$ alkoxy groups, hydroxy groups, $C_1$–$C_4$ haloalkyl groups, $C_1$–$C_4$ haloalkoxy groups, $C_1$–$C_4$ alkylthio groups, $C_1$–$C_4$ alkylsulfinyl groups, $C_1$–$C_4$ alkylsulfonyl groups, nitro groups, cyano groups, azido groups, halogen atoms and sulfamoyl groups, or having a single $C_1$–$C_3$ alkylenedioxy substituent;

$R^1$ and $R^2$ are independently selected from the group consisting of: $C_1$–$C_8$ alkyl groups; $C_1$–$C_8$ alkyl groups having at least one substituent selected from the group consisting of nitrooxy groups, $C_1$–$C_4$ alkoxy groups, $C_1$–$C_4$ nitrooxyalkoxy groups, hydroxy groups, $C_3$–$C_8$ cycloalkyl groups, aryl groups, halogen atoms, cyano groups and groups of formula —$NR^3R^4$; $C_2$–$C_6$ alkenyl groups; $C_2$–$C_6$ alkenyl groups having at least one nitrooxy substituent; $C_3$–$C_8$ cycloalkyl groups; $C_3$–$C_8$ cycloalkyl groups having at least one nitrooxy substituent; and heterocyclic groups;

provided that at least one of $R^1$ and $R^2$ contains at least one nitrooxy group; and $R^3$ and $R^4$ are independently selected from the group consisting of hydrogen atoms, $C_1$–$C_4$ alkyl groups, $C_1$–$C_4$ alkyl groups having at least one nitrooxy substituent, aryl groups and aralkyl groups, or $R^3$ and $R^4$, together with the nitrogen atom to which they are attached, represent a heterocyclic group;

and pharmaceutically acceptable acid addition salts thereof.

The invention also provides a pharmaceutical composition comprising an active compound in admixture with a pharmaceutically acceptable carrier or diluent, wherein the active compound is at least one compound selected from the group consisting of compounds of formula (1) and pharmaceutically acceptable salts thereof.

The invention still further provides a method of treating an animal, particularly a mammal, e.g. a human being, suffering from a circulatory or coronary disorder, by administering thereto an effective amount of an active compound, wherein the active compound is at least one compound selected from the group consisting of compounds of formula (I) and salts thereof.

DETAILED DESCRIPTION OF INVENTION

Where aryl groups are referred to herein, these are carbocyclic aryl groups preferably having from 6 to 14 ring carbon atoms. More preferred aryl groups have from 6 to 10 carbon atoms, e.g. the phenyl or naphthyl (1- or 2- naphthyl) groups. These aryl groups may be substituted or unsubstituted. If substituted, they have at least one substituent preferably selected from the group consisting of $C_1$-$C_4$ alkyl groups, $C_1$-$C_4$ alkoxy groups, $C_1$-$C_4$ haloalkyl groups, hydroxy groups, amino groups, mono- and di- alkylamino groups where the or each alkyl part is $C_1$-$C_4$, halogen atoms, cyano groups and nitro groups.

In the case of the aralkyl groups referred to herein, the aryl part is preferably as defined above, whilst the alkyl part is preferably a $C_1$-$C_3$ alkyl group (which may be straight or branched chain), more preferably a $C_1$ or $C_2$ alkyl group. The aralkyl group may contain 1 or more, preferably 1 or 2, aryl substituents on the alkyl part.

Where heterocyclic groups are referred to herein, these preferably have from 5 to 14, mo e preferably 5 to 10, ring atoms, of which from 1 to 5, more preferably 1 to 3, are hetero-atoms selected from the group consisting of nitrogen, oxygen and sulfur hetero-atoms. Such heterocyclic groups may be substituted or unsubstituted. If substituted, they have at least one substituent preferably selected from the group consisting of $C_1$-$C_4$ alkyl groups, $C_1$-$C_4$ alkoxy groups, $C_1$-$C_4$ haloalkyl groups, hydroxy groups, amino groups, mono- and di- alkylamino groups where the or each alkyl part is $C_1$-$C_4$, nitro groups, halogen atoms, aryl groups and aralkyl groups. The rings may be aromatic or non-aromatic in character. If non-aromatic, they may be fully or partially saturated.

In the compounds of the invention, Ar represents a phenyl group having one or two substituents selected from the following groups:

$C_1$-$C_4$, particularly $C_1$-$C_3$, alkyl groups, which may be straight or branched chain groups, for example the methyl, ethyl, propyl, isopropyl, butyl, isobutyl, sec-butyl or t-butyl groups, particularly the methyl, ethyl, propyl or isopropyl groups;

$C_1$-$C_4$, particularly $C_1$-$C_3$, alkoxy groups, which may be straight or branched chain groups, for example the methoxy, ethoxy, propoxy, isopropoxy, butoxy, isobutoxy, sec-butoxy or t-butoxy groups, particularly the methoxy, ethoxy, propoxy or isopropoxy groups;

the hydroxy group;

$C_1$-$C_4$, particularly $C_1$ or $C_2$, haloalkoxy groups which may have one or more halogen atoms up to (if desired) complete perhalogenation, for example the difluoromethoxy, trifluoromethoxy or 2,2-difluoroethoxy, particularly trifluoromethoxy, groups;

$C_1$-$C_4$, particularly $C_1$-$C_3$, alkylthio groups, such as the methylthio, ethylthio, propylthio, isopropylthio, butylthio, isobutylthio, sec-butylthio or t-butylthio groups, particularly the methylthio, ethylthio, propylthio or isopropylthio groups;

$C_1$-$C_4$ particularly $C_1$-$C_3$, alkylsulfinyl groups, such as the methanesulfinyl, ethanesulfinyl, propanesulfinyl, isopropanesulfinyl, butanesulfinyl, isobutanesulfinyl, sec-butanesulfinyl or t-butanesulfinyl groups, particularly the methanesulfinyl, ethanesulfinyl, propanesulfinyl or isopropanesulfinyl groups;

$C_1$-$C_4$, particularly $C_1$-$C_3$, alkylsulfonyl groups, such as the methanesulfonyl, ethanesulfonyl, propanesulfonyl, isopropanesulfonyl, butanesulfonyl, isobutanesulfonyl, sec-butanesulfonyl or t-butanesulfonyl groups, particularly the methanesulfonyl, ethanesulfonyl, propanesulfonyl or isopropanesulfonyl groups;

the nitro, cyano, azido or sulfamoyl groups; and halogen atoms, such as the fluorine, chlorine, bromine or iodine atoms.

Alternatively, the phenyl group represented by Ar may have a single substituent selected from the group consisting of $C_1$-$C_3$, particularly $C_1$ or $C_2$, alkylenedioxy groups, such as the methylenedioxy or ethylenedioxy groups.

It will be noted that, in the compounds of the invention, the phenyl group represented by Ar must be substituted. As in the prior art, compounds corresponding to those of the present invention but in which Ar represents an unsubstituted phenyl group have shown lesser activity, at least so far as concerns the activities to which the present invention relates.

Where $R^1$ or $R^2$ represents an alkyl group, this is a $C_1$-$C_8$, particularly $C_1$-$C_6$, alkyl group, which may be a straight or branched chain group and which may be unsubstituted or may have at least one nitrooxy substituent. Where the alkyl group is substituted, there is no particular upper limit to the number of nitrooxy substituents, other than that dictated by practical considerations (such as ease of preparation and steric constraints); however, one or two nitrooxy substituents, preferably 1 nitrooxy substituent, are usually preferred. Examples of such groups include the methyl, ethyl, propyl, isopropyl, butyl, isobutyl, pentyl, hexyl, heptyl and octyl groups and their nitrooxy-substituted analogs, for example the 2-nitrooxyethyl, 2-nitrooxypropyl, 3-nitrooxypropyl, 2,3-dinitrooxypropyl, 1-(nitrooxymethyl)ethyl, 2-nitrooxy-1-(nitrooxymethyl)ethyl (="1,3-dinitrooxyisopropyl"), 4-nitrooxybutyl, 2-nitrooxybutyl, 5-nitrooxypentyl and 6-nitrooxyhexyl groups.

Alternatively, where $R^1$ or $R^2$ represents an alkyl group, this may have, instead or in addition, one or more of the following substituents:

$C_1$-$C_4$, particularly $C_1$-$C_3$, alkoxy groups which may be unsubstituted or have at least one nitrooxy substituent; examples include the methoxy, ethoxy, propoxy, isopropoxy and butoxy groups and their nitrooxy-substituted analogs, particularly the methoxy, ethoxy, propoxy and 2-nitrooxyethoxy groups;

$C_3$-$C_8$ cycloalkyl groups, particularly $C_3$-$C_6$ cycloalkyl groups; for example the cyclopropyl, cyclobutyl, cyclopentyl, cyclohexyl, cycloheptyl and cyclooctyl groups, particularly the cyclopropyl, cyclobutyl, cyclopentyl and cyclohexyl groups.

aryl groups, which may be as defined above; examples include the phenyl, 1-naphthyl and 2-naphthyl groups and such groups having one or more substituents selected from the group consisting of: $C_1$-$C_4$, particularly $C_1$-$C_3$, alkyl groups, especially the methyl, ethyl, propyl or isopropyl groups; $C_1$-$C_4$, particularly $C_1$-$C_3$, alkoxy groups, especially the methoxy, ethoxy, propoxy and isopropoxy groups; and halogen atoms, such as the fluorine, chlorine, bromine or iodine atoms;

halogen atoms, such as the fluorine, chlorine, bromine or iodine atoms, and specific examples of such substituted alkyl groups include the difluoromethyl, trifluoromethyl, 2-chloroethyl. 2-bromoethyl, 2,2,2-trichloroethyl and 3-chloropropyl groups;

cyano groups, and examples of such substituted alkyl groups include the 2-cyanoethyl and 3-cyanopropyl groups; and groups of formula —NR$^3$R$^4$, in which: R$^3$ and R$^4$ are the same or different and each represents: a hydrogen atom; a C$_1$–C$_4$ alkyl group which is unsubstituted or has at least one nitrooxy substituent (for example the methyl, ethyl, propyl, isopropyl, butyl, isobutyl, 2-nitrooxyethyl, 2-nitrooxypropyl or 3-nitrooxypropyl groups); an aryl group, which is as defined above (for example any one of those aryl groups defined above in relation to substituents on alkyl groups represented by R$^1$ and R$^2$); an aralkyl group, which is as defined above (for example a benzyl, phenethyl, 3-phenylpropyl or benzhydryl group, in which the aryl part may be unsubstituted or may have one or more of those substituents defined above in relation to the aryl groups which may be substituents on alkyl groups represented by R$^1$ or R$^2$); or R$^3$ and R$^4$ may, together with the nitrogen atom to which they are attached, represent a cyclic amino group which is a heterocyclic group as defined above, for example a 1-pyrrolidinyl, piperidino, morpholino, 4-methyl-1-piperazinyl, 4-phenyl-1-piperazinyl or 4-benzhydryl-1-piperazinyl group.

Alternatively, R$^1$ or R$^2$ may represent a C$_2$–C$_6$ alkenyl, particularly C$_3$ or C$_4$ alkenyl, group which is unsubstituted or has at least one, preferably one or two, more preferably one, nitrooxy substituents and which may be a straight or branched chain group. Examples of such groups include the allyl, methallyl, 1-propenyl, 2-tutenyl and 4-nitrooxy-2-butenyl groups.

Where R$^1$ or R$^2$ represents a cycloalkyl group, this is a C$_3$–C$_8$, preferably C$_3$–C$_6$, cycloalkyl group, which may be unsubstituted or may have at least one, preferably one or two and more preferably one, nitrooxy substituents. Examples of such groups include the cyclopropyl, cyclobutyl, cyclopentyl, cyclohexyl, cycloheptyl and cyclooctyl groups and their nitrooxy-substituted analogs, particularly the cyclopropyl, cyclobutyl, cyclopentyl, cyclohexyl, 2-nitrooxycyclopentyl, 3-nitrooxycyclopentyl, 2-nitrooxycyclohexyl. 3-nitrooxycyclohexyl and 4-nitrooxycyclohexyl groups.

Where R$^1$ or R$^2$ represents a heterocyclic group, this is as defined above and examples include the 1-benzyl-3-pyrrolidinyl, 1-methyl-3-piperidyl, 1-benzyl-3-piperidyl, 1-methyl-4-piperidyl. 1-benzyl-4-piperidyl and 1-benzhydryl-3-piperidyl groups.

In selecting R$^1$ and R$^2$ from the groups defined above, it must be borne in mind that at least one of R$^1$ and R$^2$ must include at least one nitrooxy substituent and, if desired, both R$^1$ and R$^2$ may represent groups, each of which includes at least one nitrooxy substituent.

Preferred classes of compounds of the present invention are as follows:

1. Compounds of formula (I) and salts thereof, in which:

Ar represents a phenyl group having one or two substituents selected from the group consisting of nitro groups, C$_1$ or C$_2$ haloalkyl groups and halogen atoms.

2. Compounds of formula (I) and salts thereof, in which:

Ar represents a phenyl group having one or two substituents selected from the group consisting of nitro groups, trifluoromethyl groups and chlorine atoms.

3. Compounds of formula (I) and salts thereof, in which Ar represents a 2-nitrophenyl group, a 3-nitrophenyl group, a 2-trifluoromethylphenyl group, a 3-trifluoromethylphenyl group or a 2,3-dichlorophenyl group.

4. Compounds of formula (I) and salts thereof, in which:

R$^1$ and R$^2$ are independently selected from the group consisting of C$_1$–C$_6$ alkyl groups, C$_1$–C$_6$ alkyl groups having one or two nitrooxy substituents, C$_1$–C$_3$ alkyl groups having one C$_1$–C$_3$ alkoxy substituent, C$_1$–C$_3$ alkyl groups having one C$_1$–C$_3$ nitrooxyalkoxy substituent, C$_1$–C$_3$ alkyl groups having a single substituent of formula —NR$^{3a}$R$^{4a}$, where R$^{3a}$ and R$^{4a}$ are independently selected from the group consisting of hydrogen atoms, C$_1$–C$_3$ alkyl groups, C$_1$–C$_3$ nitrooxyalkyl groups and benzyl groups, or R$^{3a}$ and R$^{4a}$, together with the nitrogen atom to which they are attached, form a heterocyclic group having 5 or 6 ring atoms, of which 1 or 2, including said nitrogen atom, are hetero-atoms selected from the group consisting of nitrogen and oxygen hetero-atoms, said heterocyclic group being unsubstituted or having a single C$_1$–C$_3$ alkyl, phenyl, benzyl or benzhydryl substituent., heterocyclic groups, said heterocyclic groups having 5 or 6 ring atoms of which 1 or 2 are hetero-atoms selected from the group consisting of nitrogen and oxygen hetero-atoms, and being unsubstituted or having a single substituent selected from the group consisting of C$_1$–C$_3$ alkyl groups, phenyl groups, benzyl groups and benzhydryl groups, C$_5$ and C$_6$ cycloalkyl groups and C$_5$ and C$_6$ nitrooxycycloalkyl groups. 5. Compounds of formula (I) and salts thereof, in which:

R$^1$ and R$^2$ are independently selected from the group consisting of C$_1$–C$_6$ alkyl groups, 2-(4-phenyl-1-piperazinyl)ethyl groups, 2-(4-benzhydryl-1-piperazinyl)ethyl groups, 2-(N-benzyl-N-methylamino)ethyl groups, 1-benzyl-3-piperidyl groups, 1-benzyl-4-piperidyl groups, 1-benzhydryl-3-piperidyl groups, C$_2$–C$_6$ alkyl groups having one or two nitrooxy substituents, 2-(2-nitrooxyethoxy)ethyl groups, 2-bis(2-nitrooxyethyl)aminoethyl groups, 4-nitrooxy-2-butenyl groups, 2-nitrooxycyclopentyl groups, 4-nitrooxycyclohexyl groups and 2-nitrooxycyclohexyl groups.

6. Compounds of formula (I) and salts thereof, in which:

R$^1$ and R$^2$ are independently selected from the group consisting of methyl groups, ethyl groups, isopropyl groups, butyl groups, isobutyl groups, pentyl groups, hexyl groups, C$_2$–C$_6$ alkyl groups having one or two nitrooxy substituents, 2-(N-benzyl-N-methylamino)ethyl groups, 1 -benzyl-3-piperidyl groups, 1-benzyl-4-piperidyl groups and 1-benzhydryl-3-piperidyl groups.

7. Compounds of formula (I) and salts thereof, in which: R$^1$ and R$^2$ are independently selected from the group consisting of ethyl groups, isopropyl groups, 2-nitrooxypropyl groups, 3-nitrooxypropyl groups, 4-nitrooxybutyl groups, 5-nitrooxypentyl groups, 6-nitrooxyhexyl groups, 1-(nitrooxymethyl)ethyl groups, 2-nitrooxycyclohexyl groups, 2(N-benzyl-N-methylamino)ethyl groups, 1-benzyl-3-piperidyl groups, 1-benzyl-4-piperidyl groups and 1-benzhydryl-3-piperidyl groups.

8. Compounds of formula (I) and salts thereof, in which:

R$^1$ and R$^2$ are independently selected from the group consisting of ethyl groups, 2-nitrooxyethyl groups, 2- nitrooxypropyl groups, 3-nitrooxypropyl groups, 4-nitrooxybutyl groups, 5-nitrooxypentyl groups, 6-nitrooxyhexyl groups, 2-nitrooxycyclohexyl groups, 1-benzyl-3-piperidyl groups and 1-benzyl-4-piperidyl groups.

9. Compounds of formula (I) and salts thereof, in which Ar is as defined in 1. above and $R^1$ and $R^2$ are as defined in 4. above.

10. Compounds of formula (I) and salts thereof, in which Ar is as defined in 2. above and $R^1$ and $R^2$ are as defined in 5. above.

11. Compounds of formula (I) and salts thereof, in which Ar is as defined in 2. above and $R^1$ and $R^2$ are as defined in 6. above.

12. Compounds of formula (I) and salts thereof, in which Ar is as defined in 3. above and $R^1$ and $R^2$ are as defined in 7. above.

13. Compounds of formula (I) and salts thereof, in which Ar is as defined in 3. above and $R^1$ and $R^2$ are as defined in 8. above.

The compounds of the invention contain at least two basic nitrogen atoms and may, depending upon the nature of the substituents represented by $R^1$ and $R^2$, contain one or more additional basic amino groups. Accordingly, the compounds of the invention can form acid addition salts. The nature of such salts is not critical to the invention. Where the salts are to be employed for therapeutic purposes, however, it is, of course, important that the resulting salts should be pharmaceutically acceptable which, as is well known in the art, means that the salts should not have a reduced activity (or unacceptably reduced activity) or an increased toxicity (or unacceptably increased toxicity) as compared with the parent base. Where, however, the salts are intended for non-therapeutic use, for example as intermediates, even this restriction does not apply. Examples of acids which can form pharmaceutically acceptable acid addition salts include: mineral acids, such as hydrochloric acid, hydrobromic acid, hydroiodic acid and sulfuric acid; organic sulfonic acids, such as methanesulfonic acid, ethanesulfonic acid, p-toluenesulfonic acid and benzenesulfonic acid; and organic carboxylic acids, such as oxalic acid, maleic acid, fumaric acid, tartaric acid and citric acid.

Specific examples of compounds of formula (I) are those compounds in which Ar, $R^1$ and $R^2$ are as defined in the following Table 1. In this table, the following abbreviations are used:

| Bu | butyl |
|---|---|
| iBu | isobutyl |
| Bun | 2-butenyl |
| Bz | benzyl |
| Bzhy | benzhydryl |
| Et | ethyl |
| Hx | hexyl |
| cHx | cyclohexyl |
| Me | methyl |
| Nox | nitrooxy |
| Ph | phenyl |
| Pip | piperidyl |
| Piz | piperazinyl |
| Pn | pentyl |
| cPn | cyclopentyl |
| Pr | propyl |
| iPr | isopropyl |
| Sam | sulfamoyl |
| TFM | trifluoromethyl |

Where appropriate, the compounds of the invention are hereinafter identified by the numbers assigned to them in the following Table 1.

TABLE 1

| Cpd No | Ar | $R^1$ | $R^2$ |
|---|---|---|---|
| 1 | o-$NO_2$-Ph | Me | 2-NoxEt |
| 2 | o-$NO_2$-Ph | Me | 3-NoxPr |
| 3 | o-$NO_2$-Ph | Me | 2-NoxPr |
| 4 | o-$NO_2$-Ph | Et | 2-NoxEt |
| 5 | o-$NO_2$-Ph | Et | 3-NoxPr |
| 6 | o-$NO_2$-Ph | Et | 2-NoxPr |
| 7 | o-$NO_2$-Ph | Et | 6-NoxHx |
| 8 | o-$NO_2$-Ph | Et | $(NoxCH_2)_2CH$ |
| 9 | o-$NO_2$-Ph | Et | 2,3-diNoxPr |
| 10 | o-$NO_2$-Ph | Et | 2-[(2-NoxEt)$_2$N]Et |
| 11 | o-$NO_2$-Ph | Et | 2-(2-NoxEtO)Et |
| 12 | o-$NO_2$-Ph | Et | 4-NoxBun |
| 13 | o-$NO_2$-Ph | Et | 2-NoxcHx |
| 14 | o-$NO_2$-Ph | 2-(NMeBz)Et | 2-NoxEt |
| 15 | o-$NO_2$-Ph | 2-(NMeBz)Et | 3-NoxPr |
| 16 | o-$NO_2$-Ph | 2-(NMeBz)Et | 2-NoxPr |
| 17 | o-$NO_2$-Ph | 2-(4-Me-1-Piz)Et | 2-NoxEt |
| 18 | o-$NO_2$-Ph | 2-(4-Me-1-Piz)Et | 3-NoxPr |
| 19 | o-$NO_2$-Ph | 2-(4-Me-1-Piz)Et | 2-NoxPr |
| 20 | o-$NO_2$-Ph | 2-(4-Ph-1-Piz)Et | 2-NoxEt |
| 21 | o-$NO_2$-Ph | 2-(4-Ph-1-Piz)Et | 3-NoxPr |
| 22 | o-$NO_2$-Ph | 2-(4-Ph-1-Piz)Et | 2-NoxPr |
| 23 | o-$NO_2$-Ph | 1-Bz-3-Pip | 2-NoxEt |
| 24 | o-$NO_2$-Ph | 1-Bz-3-Pip | 3-NoxPr |
| 25 | o-$NO_2$-Ph | 1-Bz-3-Pip | 2-NoxPr |
| 26 | m-$NO_2$-Ph | Me | 2-NoxEt |
| 27 | m-$NO_2$-Ph | Me | 3-NoxPr |
| 28 | m-$NO_2$-Ph | Me | 2-NoxPr |
| 29 | m-$NO_2$-Ph | Et | 2-NoxEt |
| 30 | m-$NO_2$-Ph | Et | 3-NoxPr |
| 31 | m-$NO_2$-Ph | Et | 2-NoxPr |
| 32 | m-$NO_2$-Ph | Et | 6-NoxHx |
| 33 | m-$NO_2$-Ph | Et | $(NoxCH_2)_2CH$ |
| 34 | m-$NO_2$-Ph | Et | 2,3-diNoxPr |
| 35 | m-$NO_2$-Ph | Et | 2-[(2-NoxEt)$_2$N]Et |
| 36 | m-$NO_2$-Ph | Et | 2-(2-NoxEtO)Et |
| 37 | m-$NO_2$-Ph | Et | 4-NoxBun |
| 38 | m-$NO_2$-Ph | Et | 2-NoxcHx |
| 39 | m-$NO_2$-Ph | iPr | 2-NoxEt |
| 40 | m-$NO_2$-Ph | iPr | 3-NoxPr |
| 41 | m-$NO_2$-Ph | iPr | 2-NoxPr |
| 42 | m-$NO_2$-Ph | 2-(NMeBz)Et | 2-NoxEt |
| 43 | m-$NO_2$-Ph | 2-(NMeBz)Et | 3-NoxPr |
| 44 | m-$NO_2$-Ph | 2-(NMeBz)Et | 2-NoxPr |
| 45 | m-$NO_2$-Ph | 2-(4-Me-1-Piz)Et | 2-NoxEt |
| 46 | m-$NO_2$-Ph | 2-(4-Me-1-Piz)Et | 3-NoxPr |
| 47 | m-$NO_2$-Ph | 2-(4-Me-1-Piz)Et | 2-NoxPr |
| 48 | m-$NO_2$-Ph | 2-(4-Ph-1-Piz)Et | 2-NoxEt |
| 49 | m-$NO_2$-Ph | 2-(4-Ph-1-Piz)Et | 3-NoxPr |
| 50 | m-$NO_2$-Ph | 2-(4-Ph-1-Piz)Et | 2-NoxPr |
| 51 | m-$NO_2$-Ph | 1-Bz-3-Pip | 2-NoxEt |
| 52 | m-$NO_2$-Ph | 1-Bz-3-Pip | 3-NoxPr |
| 53 | m-$NO_2$-Ph | 1-Bz-3-Pip | 2-NoxPr |
| 54 | o-TFM-Ph | Me | 2-NoxEt |
| 55 | o-TFM-Ph | Me | 3-NoxPr |
| 56 | o-TFM-Ph | Me | 2-NoxPr |
| 57 | o-TFM-Ph | Et | 2-NoxEt |
| 58 | o-TFM-Ph | Et | 3-NoxPr |
| 59 | o-TFM-Ph | Et | 2-NoxPr |
| 60 | o-TFM-Ph | Et | 6-NoxHx |
| 61 | o-TFM-Ph | Et | $(NoxCH_2)_2CH$ |
| 62 | o-TFM-Ph | Et | 2,3-diNoxPr |
| 63 | o-TFM-Ph | Et | 2-[(2-NoxEt)$_2$N]Et |
| 64 | o-TFM-Ph | Et | 2-(2-NoxEtO)Et |
| 65 | o-TFM-Ph | Et | 4-NoxBun |
| 66 | o-TFM-Ph | Et | 2-NoxcHx |
| 67 | o-TFM-Ph | 2-(NMeBz)Et | 2-NoxEt |
| 68 | o-TFM-Ph | 2-(NMeBz)Et | 3-NoxPr |
| 69 | o-TFM-Ph | 2-(NMeBz)Et | 2-NoxPr |
| 70 | o-TFM-Ph | 1-Bz-3-Pip | 2-NoxEt |
| 71 | o-TFM-Ph | 1-Bz-3-Pip | 3-NoxPr |
| 72 | o-TFM-Ph | 1-Bz-3-Pip | 2-NoxPr |
| 73 | m-TFM-Ph | Me | 2-NoxEt |
| 74 | m-TFM-Ph | Me | 3-NoxPr |
| 75 | m-TFM-Ph | Me | 2-NoxPr |
| 76 | m-TFM-Ph | Et | 2-NoxEt |

TABLE 1-continued

| Cpd No | Ar | R¹ | R² |
| --- | --- | --- | --- |
| 77 | m-TFM-Ph | Et | 3-NoxPr |
| 78 | m-TFM-Ph | Et | 2-NoxPr |
| 79 | m-TFM-Ph | Et | 6-NoxHx |
| 80 | m-TFM-Ph | Et | (NoxCH$_2$)$_2$CH |
| 81 | m-TFM-Ph | Et | 2,3-diNoxPr |
| 82 | m-TFM-Ph | Et | 2-[(2-NoxEt)$_2$N]Et |
| 83 | m-TFM-Ph | Et | 2-(2-NoxEtO)Et |
| 84 | m-TFM-Ph | Et | 4-NoxBun |
| 85 | m-TFM-Ph | Et | 2-Nox*cHx* |
| 86 | m-TFM-Ph | 2-(NMeBz)Et | 2-NoxEt |
| 87 | m-TFM-Ph | 2-(NMeBz)Et | 3-NoxPr |
| 88 | m-TFM-Ph | 2-(NMeBz)Et | 2-NoxPr |
| 89 | m-TFM-Ph | 1-Bz-3-Pip | 2-NoxEt |
| 90 | m-TFM-Ph | 1-Bz-3-Pip | 3-NoxPr |
| 91 | m-TFM-Ph | 1-Bz-3-Pip | 2-NoxPr |
| 92 | 2,3-diClPh | Me | 2-NoxEt |
| 93 | 2,3-diClPh | Me | 3-NoxPr |
| 94 | 2,3-diClPh | Me | 2-NoxPr |
| 95 | 2,3-diClPh | Et | 2-NoxEt |
| 96 | 2,3-diClPh | Et | 3-NoxPr |
| 97 | 2,3-diClPh | Et | 2-NoxPr |
| 98 | 2,3-diClPh | Et | 6-NoxHx |
| 99 | 2,3-diClPh | Et | (NoxCH$_2$)$_2$CH |
| 100 | 2,3-diClPh | Et | 2,3-diNoxPr |
| 101 | 2,3-diClPh | Et | 2-[(2-NoxEt)$_2$N]Et |
| 102 | 2,3-diClPh | Et | 2-(2-NoxEtO)Et |
| 103 | 2,3-diClPh | Et | 4-NoxBun |
| 104 | 2,3-diClPh | Et | 2-Nox*cHx* |
| 105 | 2,3-diClPh | 2-(NMeBz)Et | 2-NoxEt |
| 106 | 2,3-diClPh | 2-(NMeBz)Et | 3-NoxPr |
| 107 | 2,3-diClPh | 2-(NMeBz)Et | 2-NoxPr |
| 108 | 2,3-diClPh | 2-(4-Me-1-Piz)Et | 2-NoxEt |
| 109 | 2,3-diClPh | 2-(4-Me-1-Piz)Et | 3-NoxPr |
| 110 | 2,3-diClPh | 2-(4-Me-1-Piz)Et | 2-NoxPr |
| 111 | 2,3-diClPh | 2-(4-Ph-1-Piz)Et | 2-NoxEt |
| 112 | 2,3-diClPh | 2-(4-Ph-1-Piz)Et | 3-NoxPr |
| 113 | 2,3-diClPh | 2-(4-Ph-1-Piz)Et | 2-NoxPr |
| 114 | 2,3-diClPh | 1-Bz-3-Pip | 2-NoxEt |
| 115 | 2,3-diClPh | 1-Bz-3-Pip | 3-NoxPr |
| 116 | 2,3-diClPh | 1-Bz-3-Pip | 2-NoxPr |
| 117 | m-CN-Ph | Et | 2-NoxEt |
| 118 | m-CN-Ph | Et | 3-NoxPr |
| 119 | m-CN-Ph | Et | 2-NoxPr |
| 120 | m-OH-Ph | Et | 3-NoxPr |
| 121 | 3,4-diMeOPh | Et | 3-NoxPr |
| 122 | m-Sam-Ph | Et | 2-NoxPr |
| 123 | 4-Cl-3-SamPh | Et | 2-NoxPr |
| 124 | o-NO$_2$-Ph | 2-NoxEt | Me |
| 125 | o-NO$_2$-Ph | 3-NoxPr | Me |
| 126 | o-NO$_2$-Ph | 2-NoxPr | Me |
| 127 | o-NO$_2$-Ph | 2-NoxEt | Et |
| 128 | o-NO$_2$-Ph | 3-NoxPr | Et |
| 129 | o-NO$_2$-Ph | 2-NoxPr | Et |
| 130 | o-NO$_2$-Ph | 6-NoxHx | Et |
| 131 | o-NO$_2$-Ph | (NoxCH$_2$)$_2$CH | Et |
| 132 | o-NO$_2$-Ph | 2,3-diNoxPr | Et |
| 133 | o-NO$_2$-Ph | 2-NoxEt | 2-(NMeBz)Et |
| 134 | o-NO$_2$-Ph | 3-NoxPr | 2-(NMeBz)Et |
| 135 | o-NO$_2$-Ph | 2-NoxPr | 2-(NMeBz)Et |
| 136 | o-NO$_2$-Ph | 2-NoxEt | 1-Bz-3-Pip |
| 137 | o-NO$_2$-Ph | 3-NoxPr | 1-Bz-3-Pip |
| 138 | o-NO$_2$-Ph | 2-NoxPr | 1-Bz-3-Pip |
| 139 | m-NO$_2$-Ph | 2-NoxEt | Me |
| 140 | m-NO$_2$-Ph | 3-NoxPr | Me |
| 141 | m-NO$_2$-Ph | 2-NoxPr | Me |
| 142 | m-NO$_2$-Ph | 2-NoxEt | Et |
| 143 | m-NO$_2$-Ph | 3-NoxPr | Et |
| 144 | m-NO$_2$-Ph | 2-NoxPr | Et |
| 145 | m-NO$_2$-Ph | 6-NoxHx | Et |
| 146 | m-NO$_2$-Ph | (NoxCH$_2$)$_2$CH | Et |
| 147 | m-NO$_2$-Ph | 2,3-diNoxPr | Et |
| 148 | m-NO$_2$-Ph | 3-NoxPr | 2-CN-Et |
| 149 | m-NO$_2$-Ph | 2-NoxEt | 2-(NMeBz)Et |
| 150 | m-NO$_2$-Ph | 3-NoxPr | 2-(NMeBz)Et |
| 151 | m-NO$_2$-Ph | 2-NoxPr | 2-(NMeBz)Et |
| 152 | m-NO$_2$-Ph | 2-NoxEt | 1-Bz-3-Pip |
| 153 | m-NO$_2$-Ph | 3-NoxPr | 1-Bz-3-Pip |
| 154 | m-NO$_2$-Ph | 2-NoxPr | 1-Bz-3-Pip |
| 155 | o-TFM-Ph | 2-NoxEt | Me |
| 156 | o-TFM-Ph | 3-NoxPr | Me |
| 157 | o-TFM-Ph | 2-NoxPr | Me |
| 158 | o-TFM-Ph | 2-NoxEt | Et |
| 159 | o-TFM-Ph | 3-NoxPr | Et |
| 160 | o-TFM-Ph | 2-NoxPr | Et |
| 161 | o-TFM-Ph | 6-NoxHx | Et |
| 162 | o-TFM-Ph | (NoxCH$_2$)$_2$CH | Et |
| 163 | o-TFM-Ph | 2,3-diNoxPr | Et |
| 164 | o-TFM-Ph | 2-NoxEt | 2-(NMeBz)Et |
| 165 | o-TFM-Ph | 3-NoxPr | 2-(NMeBz)Et |
| 166 | o-TFM-Ph | 2-NoxPr | 2-(NMeBz)Et |
| 167 | m-TFM-Ph | 2-NoxEt | Me |
| 168 | m-TFM-Ph | 3-NoxPr | Me |
| 169 | m-TFM-Ph | 2-NoxPr | Me |
| 170 | m-TFM-Ph | 2-NoxEt | Et |
| 171 | m-TFM-Ph | 3-NoxPr | Et |
| 172 | m-TFM-Ph | 2-NoxPr | Et |
| 173 | m-TFM-Ph | 6-NoxHx | Et |
| 174 | m-TFM-Ph | (NoxCH$_2$)$_2$CH | Et |
| 175 | m-TFM-Ph | 2,3-diNoxPr | Et |
| 176 | m-TFM-Ph | 2-NoxEt | 2-(NMeBz)Et |
| 177 | m-TFM-Ph | 3-NoxPr | 2-(NMeBz)Et |
| 178 | m-TFM-Ph | 2-NoxPr | 2-(NMeBz)Et |
| 179 | m-TFM-Ph | 2-NoxEt | 1-Bz-3-Pip |
| 180 | m-TFM-Ph | 3-NoxPr | 1-Bz-3-Pip |
| 181 | m-TFM-Ph | 2-NoxPr | 1-Bz-3-Pip |
| 182 | 2,3-diClPh | 2-NoxEt | Me |
| 183 | 2,3-diClPh | 3-NoxPr | Me |
| 184 | 2,3-diClPh | 2-NoxPr | Me |
| 185 | 2,3-diClPh | 2-NoxEt | Et |
| 186 | 2,3-diClPh | 3-NoxPr | Et |
| 187 | 2,3-diClPh | 2-NoxPr | Et |
| 188 | 2,3-diClPh | 6-NoxHx | Et |
| 189 | 2,3-diClPh | (NoxCH$_2$)$_2$CH | Et |
| 190 | 2,3-diClPh | 2,3-diNoxPr | Et |
| 191 | 2,3-diClPh | 2-NoxEt | 2-(NMeBz)Et |
| 192 | 2,3-diClPh | 3-NoxPr | 2-(NMeBz)Et |
| 193 | 2,3-diClPh | 2-NoxPr | 2-(NMeBz)Et |
| 194 | 2,3-diClPh | 2-NoxEt | 1-Bz-3-Pip |
| 195 | 2,3-diClPh | 3-NoxPr | 1-Bz-3-Pip |
| 196 | 2,3-diClPh | 2-NoxPr | 1-Bz-3-Pip |
| 197 | o-NO$_2$-Ph | 2-NoxEt | 2-NoxEt |
| 198 | o-NO$_2$-Ph | 3-NoxPr | 3-NoxPr |
| 199 | o-NO$_2$-Ph | 2-NoxEt | 3-NoxPr |
| 200 | o-NO$_2$-Ph | 3-NoxPr | 2-NoxEt |
| 201 | o-NO$_2$-Ph | 3-NoxPr | 6-NoxHx |
| 202 | o-NO$_2$-Ph | 6-NoxHx | 3-NoxPr |
| 203 | o-NO$_2$-Ph | 3-NoxPr | (NoxCH$_2$)$_2$CH |
| 204 | o-NO$_2$-Ph | 2-NoxPr | 2-NoxEt |
| 205 | o-NO$_2$-Ph | 2-NoxPr | 2-NoxPr |
| 206 | o-NO$_2$-Ph | 2-NoxPr | 3-NoxPr |
| 207 | o-NO$_2$-Ph | (NoxCH$_2$)$_2$CH | 2-NoxEt |
| 208 | o-NO$_2$-Ph | (NoxCH$_2$)$_2$CH | 3-NoxPr |
| 209 | o-NO$_2$-Ph | 2-NoxPr | 2-NoxPr |
| 210 | o-NO$_2$-Ph | 2-NoxPr | 3-NoxBu |
| 211 | o-NO$_2$-Ph | 2,3-diNoxPr | 3-NoxPr |
| 212 | o-NO$_2$-Ph | 3-NoxPr | 2-NoxPr |
| 213 | m-NO$_2$Ph | 2-NoxEt | 2-NoxEt |
| 214 | m-NO$_2$Ph | 3-NoxPr | 3-NoxPr |
| 215 | m-NO$_2$Ph | 2-NoxEt | 3-NoxPr |
| 216 | m-NO$_2$Ph | 3-NoxPr | 2-NoxEt |
| 217 | m-NO$_2$Ph | 3-NoxPr | 6-NoxHx |
| 218 | m-NO$_2$Ph | 6-NoxHx | 3-NoxPr |
| 219 | m-NO$_2$Ph | 3-NoxPr | (NoxCH$_2$)$_2$CH |
| 220 | m-NO$_2$Ph | 2-NoxPr | 2-NoxEt |
| 221 | m-NO$_2$Ph | 2-NoxPr | 2-NoxPr |
| 222 | m-NO$_2$Ph | 2-NoxPr | 3-NoxPr |
| 223 | m-NO$_2$Ph | (NoxCH$_2$)$_2$CH | 2-NoxEt |
| 224 | m-NO$_2$Ph | (NoxCH$_2$)$_2$CH | 3-NoxPr |
| 225 | m-NO$_2$Ph | 2-NoxPr | 2-NoxPr |
| 226 | m-NO$_2$Ph | 2-NoxPr | 3-NoxBu |
| 227 | m-NO$_2$Ph | 2,3-diNoxPr | 3-NoxPr |
| 228 | m-NO$_2$Ph | 3-NoxPr | 2-NoxPr |
| 229 | o-TFM-Ph | 2-NoxEt | 2-NoxEt |
| 230 | o-TFM-Ph | 3-NoxPr | 3-NoxPr |
| 231 | o-TFM-Ph | 2-NoxEt | 3-NoxPr |
| 232 | o-TFM-Ph | 3-NoxPr | 2-NoxEt |
| 233 | o-TFM-Ph | 3-NoxPr | 6-NoxHx |
| 234 | o-TFM-Ph | 3-NoxPr | (NoxCH$_2$)$_2$CH |
| 235 | o-TFM-Ph | 3-NoxPr | 2-NoxPr |
| 236 | m-TFM-Ph | 2-NoxEt | 2-NoxEt |

TABLE 1-continued

| Cpd No | Ar | R¹ | R² |
|---|---|---|---|
| 237 | m-TFM-Ph | 3-NoxPr | 3-NoxPr |
| 238 | m-TFM-Ph | 2-NoxEt | 3-NoxPr |
| 239 | m-TFM-Ph | 3-NoxPr | 2-NoxEt |
| 240 | m-TFM-Ph | 3-NoxPr | 6-NoxHx |
| 241 | m-TFM-Ph | 3-NoxPr | (NoxCH₂)₂CH |
| 242 | m-TFM-Ph | 3-NoxPr | 2-NoxPr |
| 243 | 2,3-diClPh | 2-NoxEt | 2-NoxEt |
| 244 | 2,3-diClPh | 3-NoxPr | 3-NoxPr |
| 245 | 2,3-diClPh | 2-NoxEt | 3-NoxPr |
| 246 | 2,3-diClPh | 3-NoxPr | 2-NoxEt |
| 247 | 2,3-diClPh | 3-NoxPr | 6-NoxHx |
| 248 | 2,3-diClPh | 3-NoxPr | (NoxCH₂)₂CH |
| 249 | 2,3-diClPh | 2-NoxPr | 3-NoxPr |
| 250 | 2,3-diClPh | 3-NoxPr | 2-NoxPr |
| 251 | m-CN-Ph | 2-NoxEt | 2-NoxEt |
| 252 | m-CN-Ph | 3-NoxPr | 3-NoxPr |
| 253 | m-CN-Ph | 2-NoxEt | 3-NoxPr |
| 254 | m-CN-Ph | 3-NoxPr | 2-NoxEt |
| 255 | m-CN-Ph | 3-NoxPr | 6-NoxHx |
| 256 | m-CN-Ph | 3-NoxPr | (NoxCH₂)₂CH |
| 257 | m-CN-Ph | 3-NoxPr | 2-NoxPr |
| 258 | 4-Cl-3-SamPh | 2-NoxEt | 2-NoxEt |
| 259 | 4-Cl-3-SamPh | 3-NoxPr | 3-NoxPr |
| 260 | 4-Cl-3-SamPh | 3-NoxPr | 2-NoxPr |
| 261 | m-SamPh | 2-NoxEt | 2-NoxEt |
| 262 | m-SamPh | 3-NoxPr | 3-NoxPr |
| 263 | m-SamPh | 3-NoxPr | 2-NoxPr |
| 264 | p-SamPh | 2-NoxEt | 2-NoxEt |
| 265 | p-SamPh | 3-NoxPr | 3-NoxPr |
| 266 | p-SamPh | 3-NoxPr | 2-NoxPr |
| 267 | m-NO₂-Ph | 3-NoxPr | 2-(4-Bzhy-1-Piz)Et |
| 268 | m-NO₂-Ph | 3-NoxPr | 1-Bzhy-3-Pip |
| 269 | m-NO₂-Ph | 3-NoxPr | 2-NoxcHx |
| 270 | m-NO₂-Ph | 1-Bz-3-Pip | 4-NoxBu |
| 271 | m-NO₂-Ph | 1-Bz-3-Pip | 5-NoxPn |
| 272 | m-NO₂-Ph | 1-Bz-3-Pip | 6-NoxHx |
| 273 | m-NO₂-Ph | 1-Bz-3-Pip | 2-NoxcHx |
| 274 | m-NO₂-Ph | 2-(NMeBz)Et | 6-NoxHx |
| 275 | 2,3-diClPh | 3-NoxPr | 1-Bzhy-3-Pip |
| 276 | 2,3-diClPh | 1-Bz-3-Pip | 6-NoxHx |
| 277 | o-NO₂-Ph | 1-Bz-3-Pip | 6-NoxHx |
| 278 | m-NO₂-Ph | iPr | 2-NoxcHx |
| 279 | m-NO₂-Ph | iPr | 3-NoxcHx |
| 280 | m-NO₂-Ph | iPr | 4-NoxcHx |
| 281 | m-NO₂-Ph | Hx | 2-NoxcHx |
| 282 | m-NO₂-Ph | Hx | 3-NoxcHx |
| 283 | m-NO₂-Ph | Hx | 4-NoxcHx |
| 284 | m-NO₂-Ph | 2-NoxcHx | Et |
| 285 | m-NO₂-Ph | 2-NoxcHx | iPr |
| 286 | m-NO₂-Ph | 3-NoxcHx | iPr |
| 287 | m-NO₂-Ph | 4-NoxcHx | iPr |
| 288 | m-NO₂-Ph | 2-NoxcHx | Hx |
| 289 | m-NO₂-Ph | 3-NoxcHx | Hx |
| 290 | m-NO₂-Ph | 4-NoxcHx | Hx |
| 291 | m-NO₂-Ph | 2-NoxcHx | 6-NoxHx |
| 292 | m-NO₂-Ph | 4-NoxcHx | 6-NoxHx |
| 293 | m-NO₂-Ph | 6-NoxHx | iPr |
| 294 | m-NO₂-Ph | 6-NoxHx | 6-NoxHx |
| 295 | m-NO₂-Ph | 1-Me-2-(NMeBz)Et | 6-NoxHx |
| 296 | m-NO₂-Ph | 2-(NMeBz)Pr | 6-NoxHx |
| 297 | o-NO₂-Ph | iPr | 2-NoxcHx |
| 298 | o-NO₂-Ph | iPr | 4-NoxcHx |
| 299 | o-NO₂-Ph | 2-NoxcHx | Et |
| 300 | o-NO₂-Ph | 2-NoxcHx | iPr |
| 301 | o-NO₂-Ph | 2-NoxcHx | Hx |
| 302 | o-NO₂-Ph | 4-NoxcHx | iPr |
| 303 | o-TFM-Ph | iPr | 2-NoxcHx |
| 304 | o-TFM-Ph | iPr | 4-NoxcHx |
| 305 | o-TFM-Ph | 2-NoxcHx | Et |
| 306 | o-TFM-Ph | 2-NoxcHx | iPr |
| 307 | o-TFM-Ph | 2-NoxcHx | Hx |
| 308 | o-TFM-Ph | 4-NoxcHx | iPr |
| 309 | m-TFM-Ph | iPr | 2-NoxcHx |
| 310 | m-TFM-Ph | iPr | 4-NoxcHx |
| 311 | m-TFM-Ph | Hx | 2-NoxcHx |
| 312 | m-TFM-Ph | Hx | 4-NoxcHx |
| 313 | m-TFM-Ph | 2-NoxcHx | Et |
| 314 | m-TFM-Ph | 2-NoxcHx | iPr |
| 315 | m-TFM-Ph | 4-NoxcHx | iPr |
| 316 | 2,3-diClPh | iPr | 2-NoxcHx |
| 317 | 2,3-diClPh | iPr | 4-NoxcHx |
| 318 | 2,3-diClPh | Hx | 2-NoxcHx |
| 319 | 2,3-diClPh | Hx | 4-NoxcHx |
| 320 | 2,3-diClPh | 2-NoxcHx | Et |
| 321 | 2,3-diClPh | 2-NoxcHx | iPr |
| 322 | 2,3-diClPh | 4-NoxcHx | iPr |
| 323 | 2,3-diClPh | 2-NoxcHx | Hx |
| 324 | 2,3-diClPh | 4-NoxcHx | Hx |
| 325 | 2,3-diClPh | 2-NoxcHx | 6-NoxHx |
| 326 | 2,3-diClPh | 4-NoxcHx | 6-NoxHx |
| 327 | 2,3-diClPh | 6-NoxHx | iPr |
| 328 | 2,3-diClPh | 6-NoxHx | 6-NoxHx |
| 329 | 2,3-diClPh | 1-Me-2-(NMeBz)Et | 6-NoxHx |
| 330 | 2,3-diClPh | 2-(NMeBz)Et | 6-NoxHx |
| 331 | m-NO₂-Ph | Et | 2-NoxcPn |
| 332 | m-NO₂-Ph | Et | 3-NoxcPn |
| 333 | m-NO₂-Ph | iPr | 6-NoxHx |
| 334 | m-NO₂-Ph | Bu | 3-NoxPr |
| 335 | m-NO₂-Ph | Bu | 2-NoxPr |
| 336 | m-NO₂-Ph | Bu | 6-NoxHx |
| 337 | m-NO₂-Ph | Bu | 2-NoxcHx |
| 338 | m-NO₂-Ph | Pn | 3-NoxPr |
| 339 | m-NO₂-Ph | Pn | 2-NoxPr |
| 340 | m-NO₂-Ph | Pn | 6-NoxHx |
| 341 | m-NO₂-Ph | Pn | 2-NoxcHx |
| 342 | m-NO₂-Ph | Hx | 3-NoxPr |
| 343 | m-NO₂-Ph | Hx | 2-NoxPr |
| 344 | m-NO₂-Ph | Hx | 6-NoxHx |
| 345 | m-NO₂-Ph | 6-NoxHx | Bu |
| 346 | m-NO₂-Ph | 2-NoxcHx | Bu |
| 347 | m-NO₂-Ph | 6-NoxHx | Pn |
| 348 | m-NO₂-Ph | 2-NoxcHx | Pn |
| 349 | m-NO₂-Ph | 6-NoxHx | Hx |
| 350 | 2,3-diClPh | iPr | 3-NoxPr |
| 351 | 2,3-diClPh | iPr | 2-NoxPr |
| 352 | 2,3-diClPh | iPr | 6-NoxHx |
| 353 | 2,3-diClPh | Hx | 3-NoxPr |
| 354 | 2,3-diClPh | Hx | 2-NoxPr |
| 355 | 2,3-diClPh | Hx | 6-NoxHx |
| 356 | o-NO₂-Ph | iPr | 6-NoxHx |
| 357 | m-TFM-Ph | iPr | 6-NoxHx |
| 358 | m-NO₂-Ph | Me | 2-NoxcHx |
| 359 | m-NO₂-Ph | Me | 6-NoxHx |
| 360 | m-NO₂-Ph | iBu | 2-NoxcHx |
| 361 | m-NO₂-Ph | 6-NoxHx | Me |
| 362 | m-NO₂-Ph | 2-NoxcHx | Me |
| 363 | m-NO₂-Ph | 2-NoxcHx | iBu |
| 364 | m-NO₂-Ph | 1-Bz-4-Pip | 4-NoxBu |
| 365 | m-NO₂-Ph | 1-Bz-4-Pip | 5-NoxPn |
| 366 | m-NO₂-Ph | 1-Bz-4-Pip | 6-NoxHx |
| 367 | m-NO₂-Ph | 1-Bz-4-Pip | 2-NoxcHx |
| 368 | 2,3-diClPh | 1-Bz-4-Pip | 6-NoxHx |
| 369 | 2,3-diClPh | 1-Bz-4-Pip | 2-NoxcHx |

Of the compounds listed above, preferred compounds are Compounds Nos. 31, 32, 33, 38, 40, 43, 52, 53, 58, 77, 78, 96, 96, 106, 115, 200, 228, 249, 250, 268, 269, 270, 271, 272 and 273 and the more preferred compounds are Compound Nos. 31, 32, 38, 52, 53, 96, 97, 200, 228, 250, 269, 270, 271 and 272, that is to say:

31. 3-ethyl 5-(2-nitrooxypropyl) 2-amino-1,4-dihydro-6-methyl-4-(3nitrophenyl) pyridine-3,5-dicarboxylate 32. 3ethyl 5-(6-nitrooxyhexyl) 2-amino-1,4-dihydro-6-methyl-4-(3-nitrophenyl) pyridine-3,5-dicarboxylate 38. 3-ethyl 5-(2-nitrooxycyclohexyl) 2-amino-1,4-dihydro-6-methyl-4-(3-nitrophenyl) pyridine-3,5-dicarboxylate 52. 3-(1-benzyl-3-piperidyl) 5-(3-nitrooxypropyl)2-amino-1,4-dihydro-6-methyl-4-(3-nitrophenyl)pyridine-3,5-dicarboxylate 53. 3-(1-benzyl-3-piperidyl) 5-(2-nitrooxypropyl) 2-amino-1,4-dihydro-6-methyl-4-(3-nitrophenyl)pyridine-3,5-dicarboxylate 96. 3-ethyl 5-(3-nitrooxypropyl) 2-amino-1,4-dihydro-6-methyl-4-(2,3-dichlorophenyl) pyridine-3,5-dicarboxylate 97. 3-ethyl 5-(2-nitrooxypropyl) 2-amino-1,4-dihydro-6-methyl-4-(2,3-dichlorophenyl) pyridine-3,5-dicarboxylate 200. 3-(3-nitrooxypropyl) 5-(2-nitrooxyethyl) 2-amino-1,4-dihydro-6-methyl-4-(2-nitrophenyl)pyridine-3,5dicarboxylate 228. 3-(3-nitrooxypropyl) 5-(2-nitrooxypropyl) 2-amino-1,4-dihydro-6-methyl-4-(3-nitrophenyl)pyridine-3,5-dicarboxylate 250. 3-(3-nitrooxypropyl) 5-2-nitrooxypropyl) 2-amino-1,4-dihydro-6-methyl-4-(2,3-dichlorophenyl)-pyridine-3,5-dicarboxylate 269. 3-(3-nitrooxypropyl) 5-(2-nitrooxycyclohexyl) 2-amino-1,4-dihydro-6-methyl-4-(3-nitrophenyl)pyridine-3,5-dicarboxylate 270. 3-(1benzyl-3-piperidyl) 5-(4-nitrooxybutyl) 2-amino-1,4-dihydro-6-methyl-4-(3-nitrophenyl)pyridine-3,5-dicarboxylate 271. 3-(1-benzyl-3-piperidyl) 5-(5-nitrooxypentyl) 2-amino-1,4-dihydro-6-methyl-4-(3-nitrophenyl)pyridine-3,5-dicarboxylate 272. 3-(1-benzyl-3-piperidyl) 5-(6-nitrooxyhexyl) 2-amino-1,4-dihydro-6-methyl-4-(3-nitrophenyl)pyridine-3,5-dicarboxylate
and pharmaceutically acceptable acid addition salts thereof, especially the hydrochlorides.

Compounds of the invention can be prepared by condensing an α-(substituted benzylidene)acetoacetic acid ester of formula (II):

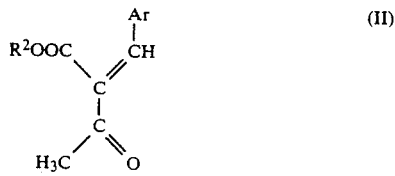

(in which Ar and $R^2$ are as defined above) with an amidinoacetic acid ester of formula (III):

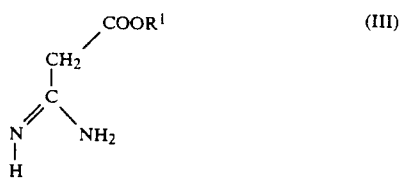

(in which $R^1$ is as defined above).

The reaction can be effected by simply mixing the two esters of formulae (II) and (III) under appropriate conditions. There is no particular criticality as to the relative proportions of the two esters; however, since equimolar amounts are involved in the reaction, in order to avoid waste, it is preferred that equimolar amounts should be used. The reaction may be effected in the presence or absence of a solvent, the nature of which is not critical, provided that it has no adverse effect upon the reaction. Suitable solvents include, for example: lower alcohols, such as ethanol, isopropanol or t-butanol; ethers, such as dioxane; lower fatty acid amides, such as dimethylformamide or dimethylacetamide; sulfoxides, such as dimethyl sulfoxide; lower aliphatic nitriles, such as acetonitrile; water; or a mixture of two or more of these solvents. The organic solvents are preferred.

The reaction will take place over a wide range of temperatures and we generally find it convenient to carry out the reaction at room temperature or with heating, for example up to the boiling point of the solvent employed. The pressure under which the reaction is carried out is likewise not critical and generally atmospheric or superatmospheric pressure may be employed.

In a preferred embodiment of the process of the invention, the reaction is carried out in an organic solvent at about the boiling point of the organic solvent and under atmospheric pressure. The time required for the reaction may vary widely, depending upon many factors, notably the reaction temperature; however, under these preferred conditions, a period of from 30 minutes to 5 hours will normally suffice.

The compound of formula (III) may be, and preferably is, employed in the form of an acid addition salt, for example a salt with hydrochloric acid, hydrobromic acid or acetic acid. Where such a salt is used, we prefer that a base, for example an alkali metal alkoxide (such as sodium methoxide or sodium ethoxide) should be added to the reaction mixture, preferably in an amount equimolar with respect to the salt of the compound of formula (III).

After completion of the reaction, the desired compound of formula (I) may be recovered from the reaction mixture by conventional means and, if necessary, further purified by such conventional techniques as recrystallization or the various chromatography techniques, particularly column chromatography.

The esters of formulae (II) and (III) are similar to known compounds and may be prepared by known techniques.

For example, compounds of formula (II) can be prepared by dehydrative condensation, for example between an aldehyde of formula Ar—CHO and an acetoacetic acid ester of formula $H_3C \cdot CO \cdot CH_2 \cdot COOR^2$, by known means [for example, G. Jones "Knoevenagel Condensation" Organic Reactions, 15, 204 (1967)]. The acetoacetic acid esters used in this reaction can be prepared from diketene and an alcohol of formula $R^2$—OH by known means, for example as described in Japanese Patent Application Kokai (i.e. as laid upon to public inspection) No. 185562/83.

Compounds of formula (III) can be prepared by known means from cyanoacetic acid esters of formula $NC \cdot CH_2 \cdot COOR^1$ (e.g. S. M. McElvain and B. E. Tate, J. Am. Chem. Soc., 73, 2760 (1951)]. The cyanoacetic acid esters employed can be prepared by a conventional esterification reaction of cyanoacetic acid with an alcohol of formula $R^1$—OH (preferably employing acid-catalysed dehydration or dehydration in the presence of a dehydrating agent, such as dicyclohexylcarbodiimide).

Where the alcohol of formula $R^1$—OH or $R^2$—OH employed above contains a nitrooxy group in its molecule, the alcohol may be prepared, for example, by the following methods:

reaction of the corresponding halo-alcohol with silver nitrate, according to the teaching of J. Am. Chem. Soc, 75, 4078 (1953); or ring opening of an epoxide with nitrogen peroxide or nitric acid, according to the teaching of Bull. Soc. Chim. France, 1955, 974 or J. Am. Chem. Soc., 75, 4255 (1953).

The compounds of the present invention have been found to have significant CA++-blocking and antihypertensive activities, for example as shown by the following tests.

Ca++-blocking activity

An isolated rat aorta was suspended in a calcium-free and high potassium Krebs-Henseleit solution maintained at a temperature of 37° C. The contractile response of the aorta to calcium chloride in concentrations ranging from $10^{-5}$ to $10^{-2}$M was recorded by means of an isometric transducer. The dose-response curve of the aorta was obtained before and after addition of a test compound at a concentration of 5 nM. Addition of the test compound shifted the dose-response curve to the right, the magnitude of the shift depending upon the potency of the Ca++-blocking activity. The test compounds showed a significant rightwards movement and, for example, that of Compound No. 6 (see foregoing Table 1) was comparable with that of Nifedipine.

Antihypertensive activity

The test animals were spontaneously hypertensive rats aged about 15 weeks. The antihypertensive activities of the test compounds were determined in these rats as follows. Each animal was anaesthetized with sodium pentobarbital (50 mg/kg, intraperitoneally) and a polyethylene cannula was placed into the abdominal aorta by the method of Weeks and Jones [J. R. Weeks and J. A. Jones. proc. Soc. Exptl. Biol. Med., 104, 646–648 (1960)]. The other end of the cannula left the animal's body at the neck. Between 3 and 6 days after this surgery, when the animal had completely recovered from surgical stress, the aortic cannula was connected to a pressure transducer to measure blood pressure and heart rate of the animal in the conscious state.

After the blood pressure and heart rate were stabilized, a test compound suspended in a 0.3% w/v aqueous carboxymethylcellulose solution was administered by gavage. The blood pressure and heart rate were recorded every 15 minutes during the 24 hours after administration of the test compound.

The experiment was carried out with Compounds No. 31, 32, 38, 200, 228, 250, 269 and 272 (see foregoing Table 1) as well as Nifedipine.

The antihypertensive activities of all of the compounds of the invention were found to be comparable with those of Nifedipine in the magnitude of hypotension. However, the compounds of the invention showed a slower onset and longer duration of activity and thus these compounds are believed to be more favorable than Nifedipine.

Accordingly, the compounds of the invention and pharmaceutically acceptable salts thereof can be used for the treatment of cardiovascular diseases, such as hypertension, angina pectoris miocardial infarction, arrhythmia and cerebral ischemia. The compounds may be administered in any suitable form, depending upon the nature of the patient and the desired route of administration. For example, the compounds may be administered orally in the form of tablets, capsules, granules, powders or syrups. Alternatively, the compounds may be administered non-orally by, for example, subcutaneous injection, intravenous injection or suppository. The compounds may, if desired, be mixed with carriers, excipients or other auxiliary substances commonly employed in the formulation of pharmaceutical preparations, for example diluents, binders, disintegrating agents, lubricants, flavors, solubilizers and suspending agents. The dose will vary, depending upon the symptoms, age and body weight of the patient, as well as the nature and severity of the disease or disorder; however, a dose of from 3 to 300 mg per day will normally be appropriate for an adult human patient, and this may be administered in a single dose or in divided doses.

The invention is further illustrated by the following non-limiting Examples.

EXAMPLE 1

3-Ethyl 5-(3-nitrooxypropyl) 2-amino-1,4-dihydro-6-methyl-4-(3-nitrophenyl) pyridine-3,5-dicarboxylate (Compound No. 30)

400 ml of an ethanolic solution containing 14 g (41 mmoles) of 3-nitrooxypropyl 2-(3-nitrobenzylidene)acetoacetate, 6.9 g (41 mmoles) of ethyl amidinoacetate hydrochloride and 2.24 g (41 mmoles) of sodium methoxide were heated under reflux for 7 hours, The solution was then cooled, insolubles were filtered off and the ethanol was evaporated off under reduced pressure. The resulting residue was dissolved in ethyl acetate and this solution was washed with water and then dried over anhydrous sodium sulfate. The ethyl acetate was evaporated off under reduced pressure, and the resulting residue was subjected to column chromatography through silica gel, eluted with a 2:1 by volume mixture of toluene and ethyl acetate, to give 14.5 g (yield 79%) of the title compound as orange plate-like crystals, melting at 140°–141.5° C.

Nuclear Magnetic Resonance Spectrum (polysol-trade mark)

δ ppm:
1.20 (3H, triplet. J=7Hz);
1.97 (2H, quintet, J=7Hz);
2.36 (3H, singlet);
3.98–4.19 (4H, multiplet);
4.32 (2H, triplet);
4.92 (1H, singlet);
6.52–6.73 (2H. broad);
7.35–8.08 (4H. multiplet);
8.38 (1H. singlet).

Infrared Absorption Spectrum (Nujol-trade mark-mull)

$\nu_{max}$cm$^{-1}$:
3450, 3370 3310 (NH), 1695, 1670 ($CO_2$), 1630 ($ONO_2$).

Mass spectrum (m/e): 448 (M+-2).

EXAMPLE 2

Bis(3-nitrooxypropyl) 2-amino-1,4-dihydro-6-methyl-4(3-nitrophenyl)pyridine-3,5-dicarboxylate (Compound No. 214)

500 ml of an isopropanol solution containing 18.8 g (55.7 mmoles) of 3-nitrooxypropyl 2-(3-nitrobenzylidene)acetoacetate, 14.76 g (55.7 mmoles) of 3-nitrooxypropyl amidinoacetate acetate and 3.00 g (55.7 mmoles) of sodium methoxide were heated under reflux for 90 minutes. The solution was then cooled and insolubles were filtered off. The isopropanol was then evaporated off under reduced pressure. The resulting residue was dissolved in methylene chloride, and the solution was washed with water and dried over anhydrous sodium sulfate. The methylene chloride was evaporated off under reduced pressure, to give a residue, which was purified by silica gel column chromatography, eluted with a 3:1 by volume mixture of toluene and ethyl acetate, and the product was recrystallized from toluene, to afford 19.3 g (yield 65.9%) of the title compound as yellow powdery crystals, melting at 145°–146° C.

Nuclear Magnetic Resonance Spectrum (polysol) δ ppm:
1.92–2.09 (4H, multiplet);
2.33 (3H, singlet);
3.97–4.20 (4H, multiplet);
4.33–4.43 (4H, multiplet);
4.91 (1H, singlet);
6.73 (2H, broad);
7.34–8.08 (4H, multiplet);
8.47 (1H, broad).
Mass spectrum (m/e): 523 (M+-2).
Elemental Analysis:
Calculated for $C_{20}H_{23}N_5O_{12}$:
C 45.72%; H, 4.41%; N, 13.33%.
Found: C, 45.91%; H, 4.51%; N. 13.32%.

The compounds listed below were prepared by the same reactions as described in Examples 1 and 2, employing appropriate starting materials. The compounds are identified by the numbers assigned to them in the foregoing list (Table 1).

Compound No. 4: $n_D^{25} = 1.5666$.
Compound No. 6 hydrochloride, melting at 78°–81° C.
Compound No. 29, melting at 179°–180° C.
Compound No. 31, melting at 171°–173° C.
Compound No. 32, melting at 106°–108° C.
Compound No. 38, melting at 88°–91° C.
Compound No. 33, melting at 70°–73° C.
Compound No. 40, melting at 114°–115° C.
Compound No. 43: Infra Adsorption Spectrum (Nujol $\nu_{max}$cm$^{-1}$: 3420, 3300 (NH). 1670, 1640 ($CO_2$), 1620 ($ONO_2$)
Compound No. 52, melting at 62°–65° C.
Compound No. 53 dihydrochloride, melting at 135°–138° C.
Compound No. 58: Infrared Absorption Spectrum (Nujol) $\nu_{max}$cm$^{-1}$: 3450, 3320 (NH), 1710, 1670 ($CO_2$), 1630 ($ONO_2$).
Compound No. 77, melting at 20° C.
Compound No. 78, melting at 59°–61° C.
Compound No. 96, melting at 62°–64° C.
Compound No. 97, melting at 71°–73° C.
Compound No. 106 dihydrochloride, melting at 104°–106° C.
Compound No. 115, melting at 74°–77° C.
Compound No. 118, melting at 143°–144° C.
Compound No. 120, melting at 69°–71° C.
Compound No. 121, melting at 154°–155° C.
Compound No. 122, melting at 132°–134.5° C.
Compound No. 123, melting at 174°–176° C.
Compound No. 140, melting at 177°–179° C.
Compound No. 148, melting at 169°–171° C.
Compound No. 150, melting at 53°–56° C.
Compound No. 153, melting at 72°–75° C.
Compound No. 200: Infrared Absorption Spectrum (neat) $\nu_{max}$cm$^{-1}$: 3450, 3325 (NH), 1700, 1670 ($CO_2$), 1630 ($ONO_2$).
Compound No. 212, melting at 65° C.
Compound No. 216, melting at 146°–147° C.
Compound No. 217, melting at 106°–109° C.
Compound No. 219, melting at 110°–112° C.
Compound No. 222, melting at 47°–56° C.
Compound No. 228: Infrared Absorption Spectrum (neat) $\nu_{max}$cm$^{-1}$: 3450, 3350 (NH), 1710, 1670 ($CO_2$). 1630 ($ONO_2$).
Compound No. 230: Infrared Absorption Spectrum (neat) $\nu_{max}$cm$^{-1}$: 3450, 3320 (NH), 1710, 1670 ($CO_2$), 1620 ($ONO_2$).
Compound No. 249, melting at 60°–64° C.
Compound No. 250: Infrared Absorption Spectrum (neat) $\nu_{max}$cm$^{-1}$: 3475, 3350 (NH), 1710, 1670 ($CO_2$), 1630 ($ONO_2$).
Compound No. 252, melting at 160°–161° C.
Compound No. 259, melting at 181°–182° C.
Compound No, 260, melting at 124°–126° C.
Compound No. 262, melting at 153°–155° C.
Compound No. 265, melting at 55°–58° C.
Compound No. 267, melting at 137°–140° C.
Compound No. 268 dihydrochloride, melting at 165°–171° C.
Compound No. 269, melting at 65°–69° C.
Compound No 270 dihydrochloride, melting at 131°–134° C.
Compound No. 271 dihydrochloride, melting at 112°–114° C.
Compound No. 272 dihydrochloride, melting at 114°–117° C.
Compound No. 273 dihydrochloride, melting at 154°–156° C.
Compound No. 274 dihydrochloride, melting at 71°–74° C.
Compound No. 275, melting at 109°–113° C.
Compound No. 276 dihydrochloride, melting at 126°–129° C.
Compound No. 277 dihydrochloride, melting at 117°–120° C.

We claim:

1. A compound of formula (I):

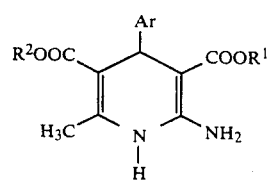

wherein
one of $R^1$ and $R^2$ is 1-benzyl-3-piperidyl and the other of $R^1$ and $R^2$ is $C_1$–$C_8$ alkyl substituted one time with nitrooxy, and
Ar is nitrophenyl,
or a pharmaceutically acceptable salt thereof.

2. The compound of claim 1 wherein $R^1$ is $C_1$–$C_8$ alkyl substituted one time with nitroxy.

3. The compound of claim 11 wherein $R^2$ is $C_1$–$C_8$ alkyl substituted one time with nitroxy.

4. The compound of claim 1 wherein the $C_1$–$C_8$ alkyl is ethyl or propyl.

5. The compound of claim 1 wherein the $C_1$–$C_8$ alkyl is a hexyl.

6. A compound as claimed in claim 1, selected from the group consisting of 3-1-benzyl-3-piperidyl) 5-(3-nitrooxypropyl) 2-amino-1,4-dihydro-6-methyl-4-(3nitrophenyl)pyridine-3,5-dicarboxylate or a pharmaceutically acceptable salt thereof.

7. A compound as claimed in claim 1, selected from the group consisting of 3-(1-benzyl-3-piperidyl) 5-(2-nitrooxypropyl) 2-amino-1,4-dihydro-6-methyl-4-(3- nitrophenyl)pyridine-3,5-dicarboxylate or a pharmaceutically acceptable salt thereof.

8. A compound as claimed in claim 1, selected from the group consisting of 3-(1-benzyl-3-piperidyl) 5-(4-nitrooxybutyl) 2-amino-1,4-dihydro-6-methyl-4-(3-nitrophenyl)pyridine-3,5-dicarboxylate or a pharmaceutically acceptable salt thereof.

9. A compound as claimed in claim 1, selected from the group consisting of 3-(1-benzyl-3-piperidyl) 5-(5-nitrooxypentyl) 2-amino-1,4-dihydro-6-methyl-4-(3-nitrophenyl)pyridine-3,5-dicarboxylate or a pharmaceutically acceptable salt thereof.

10. A compound as claimed in claim 1, selected from the group consisting of 3-(1-benzyl-3-piperidyl) 5-(6-nitrooxyhexyl) 2-amino-1,4-dihydro-6-methyl-4-(3-nitrophenyl)pyridine-3,5-dicarboxylate or a pharmaceutically acceptable salt thereof.

11. A pharmaceutical composition comprising a calcium antagonist effective amount of the compound of claim 1 or a pharmaceutically acceptable salt thereof, in a pharmaceutically acceptable carrier.

* * * * *

UNITED STATES PATENT AND TRADEMARK OFFICE
CERTIFICATE OF CORRECTION

PATENT NO.   : 4,992,451
DATED        : February 12, 1991
INVENTOR(S)  : KOIKE et al It is certified that error appears in the above-identified patent and that said Letters Patent is hereby corrected as shown below:

Column 18, line 55 (Claim 3):   replace "claim 11" with
--claim 1--.

Signed and Sealed this

Seventeenth Day of November, 1992

Attest:

DOUGLAS B. COMER

*Attesting Officer*         Acting Commissioner of Patents and Trademarks